United States Patent
Fontenelle et al.

(10) Patent No.: US 9,575,047 B2
(45) Date of Patent: Feb. 21, 2017

(54) METHOD OF CLAY STABILIZATION ANALYSIS

(71) Applicant: HALLIBURTON ENERGY SERVICES, INC., Houston, TX (US)

(72) Inventors: Lucas Kurtis Fontenelle, Porter, TX (US); Kurt William Hoeman, Houston, TX (US)

(73) Assignee: Halliburton Energy Services, Inc., Houston, TX (US)

(*) Notice: Subject to any disclaimer, the term of this patent is extended or adjusted under 35 U.S.C. 154(b) by 266 days.

(21) Appl. No.: 14/539,869

(22) Filed: Nov. 12, 2014

(65) Prior Publication Data

US 2016/0131628 A1    May 12, 2016

(51) Int. Cl.
*G01N 33/24* (2006.01)
(52) U.S. Cl.
CPC .................................... *G01N 33/24* (2013.01)
(58) Field of Classification Search
CPC ........................................................ G01N 33/24
See application file for complete search history.

(56) References Cited

U.S. PATENT DOCUMENTS

| | | | |
|---|---|---|---|
| 3,349,032 A | 10/1967 | Krieg | |
| 5,097,904 A | 3/1992 | Himes | |
| 5,149,690 A | 9/1992 | Patel et al. | |
| 2008/0207970 A1* | 8/2008 | Meurer | C10G 1/02 585/24 |
| 2013/0125630 A1* | 5/2013 | Collins | E21B 43/20 73/64.56 |

* cited by examiner

*Primary Examiner* — Laura Martin
*Assistant Examiner* — Alex Devito
(74) *Attorney, Agent, or Firm* — McAfee & Taft A Professional Corporation

(57) ABSTRACT

A method of evaluating stabilization fluids for use in a subterranean formation having a clay composition is disclosed. The method features providing a plurality of replicant core samples representative of the composition of a subterranean formation. A plurality of stabilization fluids are introduced to the plurality of replicant core sample such that an eluted mixture is extracted from a second end of each replicant core sample. Afterwards, at least one property of the eluted mixture from each replicant core sample is determined.

20 Claims, 2 Drawing Sheets

METHOD OF CLAY STABILIZATION ANALYSIS

FIELD

This disclosure relates to additives for treating subterranean formations containing clays and more particularly to evaluating additives and their effects on subterranean formations containing clays.

BACKGROUND

The production of oil and gas from subterranean formations which contain clays and other fines is often impeded by the unstable nature of these materials. Clays and fines when in an undisturbed condition are stable and cause no obstruction to the flow of hydrocarbons through the formation. However, when these materials are disturbed by contact with an aqueous fluid that is foreign to the formation, the clays can swell and the fines can migrate through the capillary flow channels in the formation resulting in a reduction of formation permeability, which is sometimes referred to herein as formation damage.

Attempts to diminish the damaging effects of introduced aqueous fluids upon subterranean formations have included treating clay contained in the formations to prevent or reduce swelling resulting from exposure to aqueous fluids. This method of control has featured the addition of various salts to the aqueous fluids utilized in the treatment of subterranean formations. Inorganic salts such as potassium chloride, calcium chloride, and ammonium chloride have been dissolved in an aqueous fluid utilized to treat a formation. The solubilized salts enter into a cation exchange with the charged layers, which comprise the clays. While these salts often do diminish the reduction of formation permeability, they can be detrimental to the performance of other constituents of the treatment fluid. For example, the salts, which are typically admixed with the aqueous fluid before admixture of any viscosifying or gelling agents to the aqueous fluid, may have a detrimental effect upon the viscosity yield by the gelling agent upon hydration in the aqueous fluid.

Furthermore, such salts, and particularly those containing chloride ions, are finding environmental objections and are therefore preferably to be avoided. Accordingly, there is interest in finding new and better additives by which a subterranean formation can be protected from the damaging effects of foreign aqueous fluids wherein the treating fluid used can be prepared simply and without detrimental effects to fluid constituents.

DETAILED DESCRIPTION

Certain embodiments will be described with reference to FIG. 1, which is not drawn to scale, and components have been exaggerated and/or simplified for illustrative purposes only. Where components of relatively well-known designs are employed, their structure and operation will not be described in detail. One of ordinary skill in the art will appreciate the many possible applications and variations of the present invention based on the following description.

In general, this disclosure relates to a method of evaluating stabilization fluids for use in a subterranean formation having a clay composition. The clay compositions are soil and rock compositions of subterranean formation that contain a clay component. Typically, this clay component will be in an amount substantial enough to be affected by aqueous fluids that are foreign to the formation, such as used in drilling, completion and other downhole petroleum recovery operations; so that, when these materials are disturbed by contact with the aqueous fluid, the clays can swell and the fines can migrate through the capillary flow channels in the formation resulting in a reduction of formation permeability or formation damage. While many different minerals can be classified as clays, in general, clays are calcium aluminum silicate materials. The addition of cations and the ratios of these materials in the clay can determine the activity when exposed to fluids deficient in the ions that the clay contains.

For downhole operations, swelling and migrating clays need to be stabilized in the subterranean formation because chemical changes, which can increase the spacing between layers in the structure of the clays, reduce the porosity and conductivity of a well under production. In traditional applications, clay swelling has been mitigated by the addition of clay stabilizers such as ionic salts, like potassium chloride, potassium iodide and sodium chloride as well as using produced water from the reservoir under treatment. However, the type and amount of stabilizer to use and the effectiveness of new stabilizing additives is difficult to determine for any particular formation because the clay composition of the formation is different for each formation and can also vary within a formation. The current method provides for a fast and accurate means of evaluating stabilization additives for use in the specific composition of the subterranean formation or reservoir and even for use in different regions of the same subterranean formation.

Figure 1:
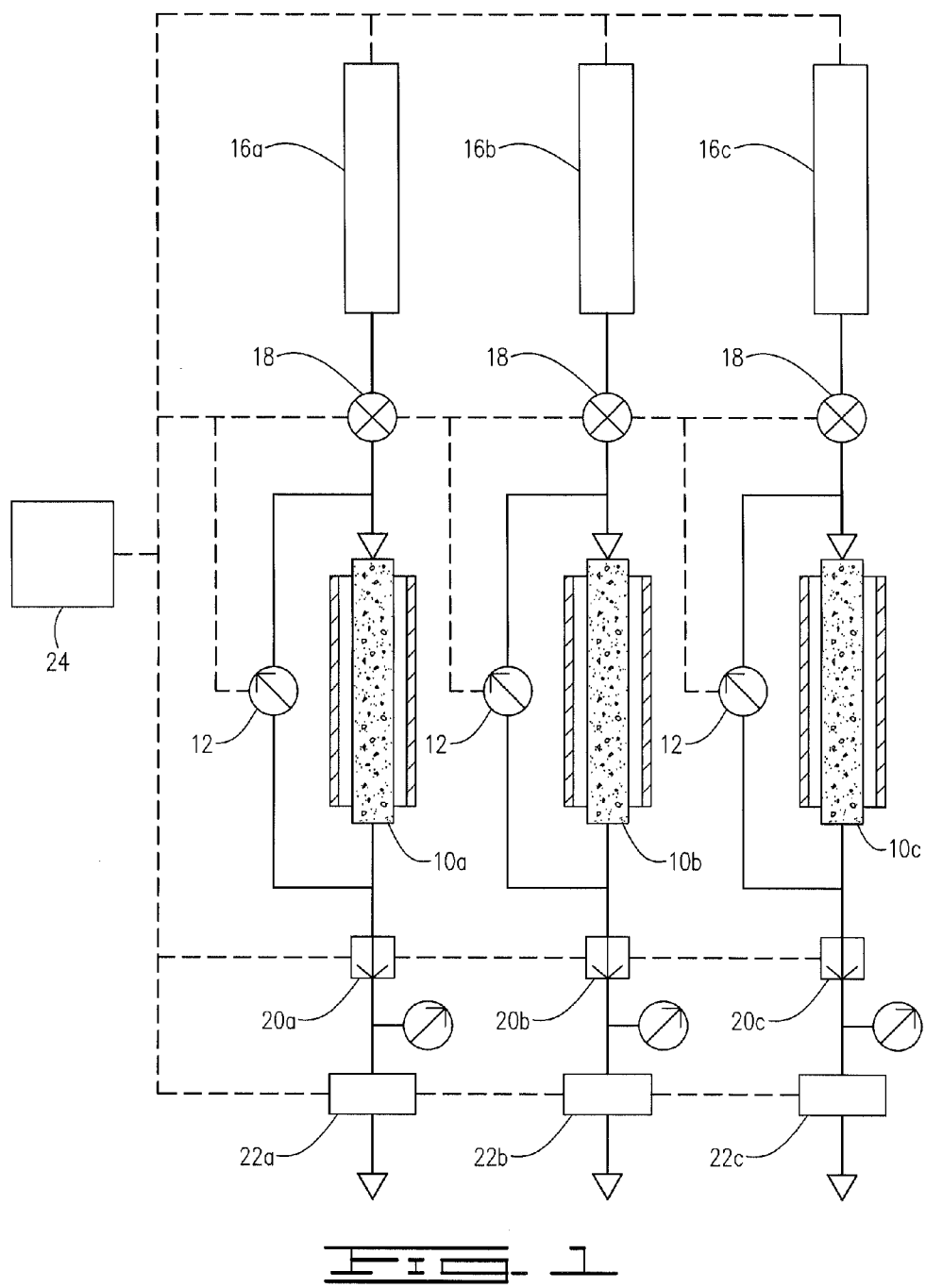
FIG. 1 is a schematic illustration of an apparatus that can be utilized in certain embodiments.

Turning now to FIG. 1, an apparatus useful for carrying out the method of evaluating stabilization fluids for use in a subterranean formation having a clay composition is illustrated. The apparatus comprises a plurality of cells or sample containers 10 for containing replicant core samples. Generally, the apparatus will comprise at least three such cells with each cell containing substantially identical replicant core samples. As used herein, the term "replicant core sample" refers to a natural or synthetic clay composition that has a composition representative of the clay composition of the subterranean formation. Replicant core samples having a natural clay composition can be core samples taken from the subject subterranean formation or can be formed from compressing well cuttings from a well extending into the subject subterranean formation into a core sample. Replicant core samples having a synthetic clay composition can be produced based on a chemical analysis of well cuttings from a well extending into the subject subterranean formation. The replicant core samples can be compressed so as to form a consolidated core or can be ground formation material, which is not consolidated into a core form. The replicant core samples can have sand or other proppant material added, as further described below.

Cells 10 are designed so that the pressure on the replicant cores cells can be increased. The pressure across the replicant cores cells can be monitored by a differential pressure transducer 12. Also, cells 10 can be heated, such as by heating sleeve 14.

At a first end, cells 10 are in fluid flow communication with fluid pump 16 capable of delivering a fluid at a constant rate. Typically, there will be plurality of fluid pumps 16 such that cells 10 are in a one-to-one relationship with the fluid pumps 16 so that a different stabilization fluid can be introduced to each cell 10. For example in FIG. 1, cell 10a is in fluid flow communication with pump 16a, cell 10b is in fluid flow communication with pump 16b, and cell 10c is in fluid flow communication with pump 16c. Fluid flow communication between cells 10 and pumps 16 is controlled by means of valve 18. Typically, there is a valve 18 per cell/pump pair.

At a second end, cell 10 is in fluid flow communication with back pressure regulator 20 and analysis device 22. Typically, there will be plurality of back pressure regulators and analysis devices 22 such that cells 10a, 10b and 10c are in a one-to-one relationship with back pressure regulators 20a, 20b and 20c and with analysis devices 22a, 22b and 22c, respectively. Back pressure regulator 20 along with pump 16 provide for maintaining a suitable pressure differential across each of the replicant core samples. Analysis device 22 can be any suitable device for determining the properties or composition of the elute coming out of the second end of cells 10. Generally, analysis device 22 comprises a spectroscopic analyzer for determining chemical concentration and comprises a balance or similar system for determining the volume of fluid extracted from the replicant core sample. For example, the spectroscopic analyzer can be an ICE technology based analyzer, such as described in U.S. Pat. No. 8,823,939.

Controller 24 can be any suitable computer and data storage type device. Controller 24 is connected to the various components described above so as to control and record temperature, differential pressure across the replicant core samples, pumping rates for pump 16, etc. Also, controller 24 controls and records the results from analysis device 22 and process the data such as to determine Darcy permeability, as described below.

In operation, the apparatus carries out a process to evaluate stabilizing additives as follows. First, replicant core samples are either obtained from the subterranean formation under evaluation or produced from well cuttings or from an analysis of the clay composition of the subterranean formation under evaluation.

The replicant core samples, all representative of the composition of the subject subterranean formation, are placed into cells 10. The cores can then be subjected to a plurality of stabilizing fluids, as explained below. Alternatively, the cores can first be compressed to a predetermined pressure. Typically, the predetermined pressure will be representative of the pressure of in the subterranean formation under evaluation; that is, typically the predetermined pressure will be determined by the overburden pressure of the subterranean formation. In some cases it may be desirable to evaluate the replicant core samples at higher pressures; thus, the predetermined pressure can be as great as the overburden pressure or higher.

Also, the replicant core samples can be heated to a predetermined temperature representative of the temperature of the subterranean formation under evaluation. In some cases it may be desirable to evaluate the replicant core samples at higher temperatures; thus, the predetermined temperature can be equal to or higher than the temperature of the subterranean formation under evaluation.

The replicant core samples are then subjected to a plurality of stabilization fluids. Typically, each replicant core sample will be subjected to a single stabilization fluid with each replicant core sample receiving a different stabilization fluid. That is, a plurality of stabilization fluids is introduced to the plurality of replicant core sample in a one-to-one relationship such that a different stabilization fluid is introduced to a first end of each of the replicant core samples. Generally, the replicant core samples will be subjected to the stabilization fluids simultaneously. The stabilizing fluids are typically an aqueous solution of a stabilizing additive. Generally, the stabilization additives are compositions, which can be used to treat the clay contained in the formation so as to lessen the swelling affects caused by introducing an aqueous well treatment fluid to the formation, and thus, diminish the reduction of formation permeability caused by aqueous well treatment fluids.

In one embodiment, at least three replicant core samples are evaluated simultaneously. The first replicant core sample is subjected to water as the stabilization fluid. The treatment water can be fresh water or a brine. The second replicant core sample is subjected to a potassium ionic salt aqueous solution as the stabilization fluid. For example, potassium chloride or potassium iodide can be the stabilizing additive of an aqueous solution. The third replicant core sample is subjected to a third stabilization fluid. The third stabilization fluid can comprise any of the various stabilization additives known in the art or can be a new stabilization fluid not previously used. The third stabilization fluid can also comprise a combination of such stabilization additives. For full benefit of the current process, the third stabilization fluid will typically not contain sodium chloride or the same potassium ionic salt used for the second stabilization fluid. Preferably, the third stabilization fluid will not contain a potassium ionic salt. Typically, the third stabilization fluid is an aqueous solution.

The stabilization fluids are delivered at a constant rate by the fluid pump 16. Generally, the fluid pump 16 can be a piston pump, syringe pump or other suitable fluid pump capable of delivering fluid at a constant rate. During delivery of the stabilization fluid, the differential pressure is measured using gauge 12 and recorded by controller 24.

The stabilization fluids are introduced to a first end of the replicant core samples under a differential pressure such that they pass through the replicant core sample and an eluted mixture is extracted from a second end of each replicant core sample. Typically, the eluted mixture will comprise stabilizing fluid and liberated clay from the replicant core sample; however, the elute mixture will generally have less of a concentration of stabilization additive because stabilization additive is retained by the replicant core sample.

Analyzing device 22 determines the volume of fluid eluted over time (flow rate) and this is recorded by controller 24. From the data recorded, controller 24 can calculate the Darcy permeability (k) of the core by the equation:

$$k = \frac{\mu\left(Q\frac{\Delta P}{L}\right)}{A}$$

Where Q is the flow rate, μ is the viscosity of the stabilization fluid, ΔP is the pressure differential, A is the cross-sectional area of the replicant core sample, and L is the length of the replicant core sample. By determining the Darcy permeability over different sequential equal time periods, a direct measurement of change in permeability as a result of each stabilizing fluid can be determined.

Also, analyzing device 22 can measure the concentration of stabilization additive in the eluded mixture using UV-Visible spectroscopy or fluorescence. From the difference in the concentration of the stabilizing additive in the stabilization fluid introduced to the replicant core sample and the eluted mixture, the minimum effective concentration of the stabilizing additive need for treatment of the subterranean formation can be determined. In one exemplary embodiment the spectroscopy is carried out utilizing ICE technology, such as described in U.S. Pat. No. 8,823,939. ICE technology utilizes optical analyzers to detect fluid components present in a sample. Light shines through a fluid sample and then through a sensor. Each sensor is programmed to recognize the chemical nature—or optical fingerprint—of a specific fluid chemical component. Measuring the intensity of light passing through any one sensor indicates the presence and proportion of a particular chemical component within the overall fluid. ICE technology does not require a computer to perform calculations on an optical spectrum. Each ICE sensor is designed to respond specifically to the fingerprint of the selected analyte or chemical component using all of the useful information in the optical spectrum. The use of an ICE technology based spectroscopy allows real-time analysis of the eluted mixture. One suitable spectroscopy utilizing ICE technology is marketed by Halliburton Engineering Services, Inc. under the trade name ICE Core technology Following treatment of the replicant core sample with stabilizing fluid, different well treatment fluids can be introduced to the first end of each replicant core sample. Based on the elute resulting from the introduction of the each well treatment fluid and effect on pressure differential, the effects of the stabilization fluid with regard to operation of specific treatment fluid on the subterranean formation can be determined. Well treatment fluids are fluids used in the completion and treatment of wellbores, such as fracking fluids. Well treatment fluids are aqueous fluids (typically fresh water or brines) containing viscosifying or gelling agents. By determining the Darcy permeability over different sequential equal time periods, a direct measurement of change in permeability as a result of the well treatment fluid for each stabilizing-fluid treated core can be determined. Additionally, the effects of the stabilizing additive retained in the replicant core sample on the viscosifying and gelling agents can be determined.

Accordingly, the method described herein allows for determining the type and concentration of stabilizing additive required for treatment of a specific subterranean formation. Since such formations are heterogeneous by nature, choosing an appropriate stabilizing additive for a specific well, or a specific interval in a well can be extremely beneficial. The method produces a direct measurement of change in permeability as a result of each stabilizing fluid imbibing into the replicant core sample, while also monitoring the concentration of migrating clays and treatment efficiency of the stabilizing fluids. Because the treatment of the cores occurs simultaneously and the system allows for high fluid throughput, results can be quickly generated providing for choosing the optimum stabilizing additive for the subterranean formation, while providing guidance on the concentration of stabilizing additive needed in the stabilizing fluid.

Figure 2:
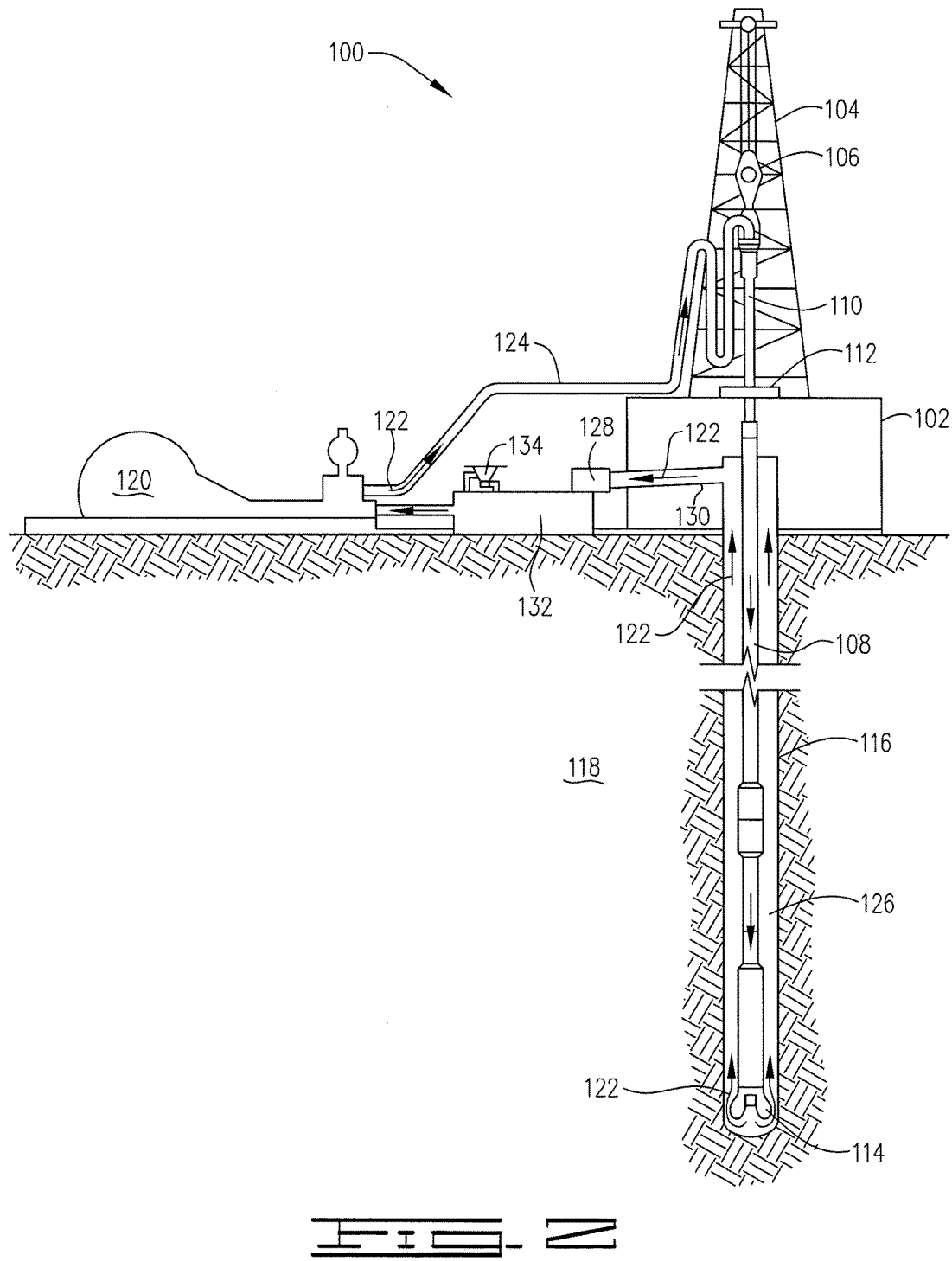
FIG. 2 is a schematic illustration generally depicting a land-based drilling assembly.

The stabilizing fluids or well treatment fluids tested in accordance with the above disclosed method may be used in down hole applications to treat wellbores and subterranean formations. They may directly or indirectly affect one or more components or pieces of equipment associated with the preparation, delivery, recapture, recycling, reuse, and/or disposal of the stabilization or well treatment fluids. For example, and with reference to FIG. 2, the stabilization or well treatment fluids may directly or indirectly affect one or more components or pieces of equipment associated with an exemplary wellbore drilling assembly 100, according to one or more embodiments. It should be noted that while FIG. 2 generally depicts a land-based drilling assembly, those skilled in the art will readily recognize that the principles described herein are equally applicable to subsea drilling operations that employ floating or sea-based platforms and rigs, without departing from the scope of the disclosure.

As illustrated, the drilling assembly 100 may include a drilling platform 102 that supports a derrick 104 having a traveling block 106 for raising and lowering a drill string 108. The drill string 108 may include, but is not limited to, drill pipe and coiled tubing, as generally known to those skilled in the art. A kelly 110 supports the drill string 108 as it is lowered through a rotary table 112. A drill bit 114 is attached to the distal end of the drill string 108 and is driven either by a downhole motor and/or via rotation of the drill string 108 from the well surface. As the bit 114 rotates, it creates a borehole 116 that penetrates various subterranean formations 118.

A pump 120 (e.g., a mud pump) circulates drilling fluid 122 through a feed pipe 124 and to the kelly 110, which conveys the drilling fluid 122 downhole through the interior of the drill string 108 and through one or more orifices in the drill bit 114. The drilling fluid 122 is then circulated back to the surface via an annulus 126 defined between the drill string 108 and the walls of the borehole 116. At the surface, the recirculated or spent drilling fluid 122 exits the annulus 126 and may be conveyed to one or more fluid processing unit(s) 128 via an interconnecting flow line 130. After passing through the fluid processing unit(s) 128, a "cleaned" drilling fluid 122 is deposited into a nearby retention pit 132 (i.e., a mud pit). While illustrated as being arranged at the outlet of the borehole 116 via the annulus 126, those skilled in the art will readily appreciate that the fluid processing unit(s) 128 may be arranged at any other location in the drilling assembly 100 to facilitate its proper function, without departing from the scope of the disclosure.

One or more of the stabilization additives or well treatment fluids tested may be added to the drilling fluid 122 via a mixing hopper 134 communicably coupled to or otherwise in fluid communication with the retention pit 132. The mixing hopper 134 may include, but is not limited to, mixers and related mixing equipment known to those skilled in the art. In other embodiments, however, the stabilization additives or well treatment fluids may be added to the drilling fluid 122 at any other location in the drilling assembly 100. In at least one embodiment, for example, there could be more than one retention pit 132, such as multiple retention pits 132 in series. Moreover, the retention pit 132 may be representative of one or more fluid storage facilities and/or units where the stabilization additives or well treatment fluids may be stored, reconditioned, and/or regulated until added to the drilling fluid 122.

As mentioned above, the stabilization or well treatment fluids may directly or indirectly affect the components and equipment of the drilling assembly 100. For example, the stabilization or well treatment fluids may directly or indirectly affect the fluid processing unit(s) 128 which may include, but is not limited to, one or more of a shaker (e.g., shale shaker), a centrifuge, a hydrocyclone, a separator (including magnetic and electrical separators), a desilter, a desander, a filter (e.g., diatomaceous earth filters), a heat exchanger, and any fluid reclamation equipment. The fluid processing unit(s) 128 may further include one or more sensors, gauges, pumps, compressors, and the like used to store, monitor, regulate, and/or recondition the stabilization or well treatment fluids.

The stabilization or well treatment fluids may directly or indirectly affect the pump 120, which representatively includes any conduits, pipelines, trucks, tubulars, and/or pipes used to fluidically convey the stabilization or well treatment fluids downhole, any pumps, compressors, or motors (e.g., topside or downhole) used to drive the stabilization or well treatment fluids into motion, any valves or related joints used to regulate the pressure or flow rate of the stabilization or well treatment fluids, and any sensors (i.e., pressure, temperature, flow rate, etc.), gauges, and/or combinations thereof, and the like. The stabilization or well treatment fluids may also directly or indirectly affect the mixing hopper 134 and the retention pit 132 and their assorted variations.

The stabilization or well treatment fluids may also directly or indirectly affect the various downhole equipment and tools that may come into contact with the stabilization or well treatment fluids such as, but not limited to, the drill string 108, any floats, drill collars, mud motors, downhole motors and/or pumps associated with the drill string 108, and any MWD/LWD tools and related telemetry equipment, sensors or distributed sensors associated with the drill string 108. The stabilization or well treatment fluids may also directly or indirectly affect any downhole heat exchangers, valves and corresponding actuation devices, tool seals, packers and other wellbore isolation devices or components, and the like associated with the wellbore 116. The stabilization or well treatment fluids may also directly or indirectly affect the drill bit 114, which may include, but is not limited to, roller cone bits, PDC bits, natural diamond bits, any hole openers, reamers, coring bits, etc.

While not specifically illustrated herein, the stabilization or well treatment fluids may also directly or indirectly affect any transport or delivery equipment used to convey the stabilization or well treatment fluids to the drilling assembly 100 such as, for example, any transport vessels, conduits, pipelines, trucks, tubulars, and/or pipes used to fluidically move the stabilization or well treatment fluids from one location to another, any pumps, compressors, or motors used to drive the stabilization or well treatment fluids into motion, any valves or related joints used to regulate the pressure or flow rate of the stabilization or well treatment fluids, and any sensors (i.e., pressure and temperature), gauges, and/or combinations thereof, and the like.

In accordance with the above description, there is provided in some embodiments a method of evaluating stabilization fluids for use in a subterranean formation having a clay composition. The method comprises the steps of:
  a. providing a plurality of replicant core samples representative of the clay composition of the subterranean formation;
  b. introducing simultaneously a plurality of stabilization fluids to the plurality of replicant core sample such that an eluted mixture is extracted from a second end of each replicant core sample;
  c. determining at least one property of the eluted mixture from each replicant core sample.

Further, the replicant core samples can be subjected to pressure at least as great as the formation pressure of the subterranean formation. In some applications the pressure can be equal to the formation pressure of the subterranean formation. In other applications the replicant core sample can be subjected to pressure greater than the formation pressure. Also, the replicant core samples can be subjected to pressure and temperature at least as great as the formation pressure and formation temperature of the subterranean formation. In some applications, the temperature can be equal to the formation temperature. In other applications, the temperature can be greater than the formation temperature.

In some applications, the replicant core is a synthetic core formulated based on a chemical analysis of at least one sample of material from the subterranean formation. In other applications, the replicant core is produce by compressing one or more samples of material from the subterranean formation. Further, the replicant core sample can include a proppant material.

In some embodiments of the method, the plurality of stabilization fluids are introduced to the plurality of replicant core sample in a one-to-one relationship such that a different stabilization fluid is introduced to a first end of each of the replicant core samples.

In some embodiments of the method, the eluted mixture has an amount of liberated clay from the replicant core sample. Also, at least one property of the eluted mixture includes a property selected from volume of eluted mixture extracted over a predetermined period of time, amount of the liberated clay present in the eluted mixture, and concentration of a stabilizing additive contained in the stabilizing elute. Further, at least one effect on the replicant core sample can be determined from the property. One effect that can be determining is the change in Darcy permeability over different sequential equal time periods. Also, the amount of stabilizing additive retained by the replicant core sample determined to thus provide the minimum concentration of stabilizing additive need for treatment of the subterranean formation.

In further embodiments of the method, there are three stabilization compounds with the first comprising fresh water or brine, the second comprising potassium chloride and the third comprising a stabilization additive other than sodium chloride and potassium chloride. That is, the third stabilization additive is substantially free of sodium chloride and potassium chloride and, preferably is substantially free of potassium ionic salts.

In yet further embodiments, the method further comprises the steps of:
  subsequent to step c, introducing a well treatment fluid to the first end of each replicant core sample; and
  determining at least one effect of the treatment fluid on each replicant core sample.

One effect that can be determining is the change in Darcy permeability over different sequential equal time periods.

A preferred embodiment of the comprises the steps of:
  a. providing a plurality of replicant core samples representative of the composition of the subterranean formation, wherein the subterranean formations has a formation temperature and formation pressure;
  b. subjecting the replicant core samples to heat and pressure representative of the formation temperature and formation pressure;
  c. introducing simultaneously a plurality of stabilization fluids to the plurality of replicant core sample in a one-to-one relationship such that a different stabilization fluid is introduced to a first end of each of the replicant core samples, and such that an eluted mixture is extracted from a second end of each replicant core sample, the eluted mixture having an amount of liberated clay from the replicant core sample;
  d. determining at least one property of the eluted mixture from each replicant core sample, wherein the at least one property includes a property selected from volume of eluted mixture extracted over a predetermined period of time, amount of liberated clay present in the eluted mixture and concentration of a stabilizing additive contained in the eluted mixture;

e. subsequent to step d, introducing a well treatment fluid to the first end of each replicant core sample; and f. determining at least one effect of the treatment fluid on each replicant core sample.

Even more preferred, is that a method with these steps utilizes three stabilization compounds with the first comprising fresh water or brine, the second comprising potassium chloride and the third comprising a stabilization additive other than sodium chloride and potassium chloride. That is, the third stabilization additive is substantially free of sodium chloride and potassium chloride and, preferably is substantially free of potassium ionic salts.

Some embodiments of the above described methods further comprise determining, from at least one property of the elute mixture, a preferred stabilization fluid for the subterranean formation. Further, these embodiment can also comprise introducing the preferred stabilization fluid into the subterranean formation through a wellbore utilizing a pump.

In other embodiments of the above described methods further comprise determining, from at least one property of the elute mixture and at least effect of the well treatment fluid, a preferred stabilization fluid for the subterranean formation and a suitable well treatment fluid for the subterranean formation. These embodiments can also comprise introducing the preferred stabilization fluid into the subterranean formation through a wellbore utilizing a pump and subsequently introducing the suitable well treatment fluid into the subterranean formation through the wellbore utilizing the pump.

Therefore, the present invention is well adapted to attain the ends and advantages mentioned, as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified, and all such variations are considered within the scope and spirit of the present invention. While compositions and methods are described in terms of "comprising," "containing," "having," or "including" various components or steps, the compositions and methods can also "consist essentially of" or "consist of" the various components and steps. Also, the terms in the claims have their plain, ordinary meaning unless otherwise explicitly and clearly defined by the patentee.

What is claimed is:

1. A method of evaluating stabilization fluids for use in a subterranean formation having a clay composition, the method comprising:
   a. providing a plurality of replicant core samples representative of the clay composition of the subterranean formation;
   b. introducing simultaneously a plurality of stabilization fluids to the plurality of replicant core sample such that an eluted mixture is extracted from a second end of each replicant core sample;
   c. determining at least one property of the eluted mixture from each replicant core sample;
   d. determining from the at least one property, a preferred stabilization fluid for the subterranean formation; and
   e. introducing the preferred stabilization fluid into the subterranean formation through a wellbore utilizing a pump.

2. The method of claim 1, wherein the subterranean formation has a formation pressure and the method further comprises:
   during step b, subjecting the replicant core samples to pressure at least as great as the formation pressure.

3. The method of claim 1, wherein the subterranean formation has a formation pressure and a formation temperature and the method further comprises:
   during step b, subjecting the replicant core samples to pressure and temperature at least as great as the formation pressure and formation temperature.

4. The method of claim 1, wherein the replicant core is a synthetic core formulated based on a chemical analysis of at least one sample of material from the subterranean formation.

5. The method of claim 1, wherein the replicant core is produced by compressing one or more samples of material from the subterranean formation.

6. The method of claim 1, wherein the replicant core includes a proppant material.

7. The method of claim 1, wherein the plurality of stabilization fluids are introduced to the plurality of replicant core sample in a one-to-one relationship such that a different stabilization fluid is introduced to a first end of each of the replicant core samples.

8. The method of claim 1, wherein the eluted mixture has an amount of liberated clay from the replicant core sample, and wherein the at least one property of the eluted mixture includes a property selected from volume of eluted mixture extracted over a predetermined period of time, amount of the liberated clay present in the eluted mixture, and concentration of a stabilizing additive contained in the stabilizing elute.

9. The method of claim 1, wherein there are three stabilization fluids with the first comprising fresh water or brine, the second comprising potassium chloride and the third comprising a stabilization additive other than sodium chloride or potassium chloride.

10. The method of claim 1, further comprising:
    subsequent to step c, introducing a well treatment fluid to the first end of each replicant core sample; and
    determining at least one effect of the treatment fluid on each replicant core sample.

11. The method of claim 10, wherein step (d) further comprises determining, from the at least one property and at least one effect, a preferred stabilization fluid for the subterranean formation and a suitable well treatment fluid for the subterranean formation.

12. The method of claim 11, further comprising, subsequent to step e, introducing the suitable well treatment fluid into the subterranean formation through the wellbore utilizing the pump.

13. A method of evaluating stabilization fluids for use in a subterranean formation having a clay composition, the method comprising:
    a. providing a plurality of replicant core samples representative of the composition of the subterranean formation, wherein the subterranean formations have a formation temperature and formation pressure;
    b. subjecting the replicant core samples to heat and pressure representative of the formation temperature and formation pressure;
    c. introducing simultaneously a plurality of stabilization fluids to the plurality of replicant core samples in a one-to-one relationship such that a different stabilization fluid is introduced to a first end of each of the replicant core samples, and such that an eluted mixture is extracted from a second end of each replicant core sample, the eluted mixture having an amount of liberated clay from the replicant core sample;

d. determining at least one property of the eluted mixture from each replicant core sample, wherein the at least one property includes a property selected from volume of eluted mixture extracted over a predetermined period of time, amount of liberated clay present in the eluted mixture and concentration of a stabilizing additive contained in the eluted mixture;

e. subsequent to step d, introducing a well treatment fluid to the first end of each replicant core sample;

f. determining at least one effect of the treatment fluid on each replicant core sample;

g. determining from the at least one property, a preferred stabilization fluid for the subterranean formation; and h. introducing the preferred stabilization fluid into the subterranean formation through a wellbore utilizing a pump.

14. The method of claim 13, wherein the replicant core samples are subjected to pressure and temperature at least as great as the formation pressure and formation temperature.

15. The method of claim 14, wherein there are three stabilization fluids with the first comprising fresh water or brine and no stabilization additive, the second comprising potassium chloride and the third comprising a stabilization additive other than sodium chloride or potassium chloride.

16. The method of claim 15, wherein the replicant core includes a proppant material.

17. The method of claim 16, wherein the replicant core is a synthetic core formulated based on a chemical analysis of at least one sample of material from the subterranean formation.

18. The method of claim 16, wherein the replicant core is produced from compressing one or more samples of material from the subterranean formation.

19. The method of claim 13, further comprising determining, from the at least one effect, a suitable well treatment fluid for the subterranean formation.

20. The method of claim 19, further comprising, subsequent to step h, introducing the suitable well treatment fluid into the subterranean formation through the wellbore utilizing the pump.

* * * * *